US008415512B2

(12) United States Patent
Sherman et al.

(10) Patent No.: US 8,415,512 B2
(45) Date of Patent: *Apr. 9, 2013

(54) HYDROCARBON CONVERSION PROCESS IMPROVEMENTS

(75) Inventors: Jeffrey H. Sherman, Vero Beach, FL (US); Eric W. McFarland, Santa Barbara, CA (US); Michael J. Weiss, Santa Barbara, CA (US); Ivan Marc Lorkovic, Santa Barbara, CA (US); Leroy E. Laverman, Santa Barbara, CA (US); Shouli Sun, Santa Barbara, CA (US); Dieter J. Schaefer, Goleta, CA (US); Galen D. Stucky, Santa Barbara, CA (US); Peter C. Ford, Santa Barbara, CA (US); Philip Grosso, Auburn, CA (US); Ashley W. Rreed, Goleta, CA (US); Michael F. Doherty, Santa Barbara, CA (US)

(73) Assignee: GRT, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/904,030

(22) Filed: Oct. 13, 2010

(65) Prior Publication Data

US 2011/0034741 A1 Feb. 10, 2011

Related U.S. Application Data

(63) Continuation of application No. 12/692,831, filed on Jan. 25, 2010, now Pat. No. 7,838,708, which is a continuation of application No. 11/098,997, filed on Apr. 5, 2005, now abandoned, which is a continuation-in-part of application No. 10/430,240, filed on Aug. 19, 2003, now Pat. No. 7,161,050, which is a continuation-in-part of application No. 10/365,346, filed on Feb. 12, 2003, now abandoned, which is a continuation of application No. 10/298,440, filed on Nov. 19, 2002, now abandoned, which is a continuation-in-part of application No. 10/208,068, filed on Jul. 29, 2002, now abandoned, which is a continuation-in-part of application No. 10/054,004, filed on Jan. 24, 2002, now Pat. No. 6,486,368, which is a continuation-in-part of application No. 09/951,739, filed on Sep. 11, 2001, now Pat. No. 6,465,696, which is a continuation-in-part of application No. 09/886,078, filed on Jun. 20, 2001, now Pat. No. 6,472,572.

(51) Int. Cl.
C07C 27/00 (2006.01)
C07C 27/10 (2006.01)

(52) U.S. Cl.
USPC ........... 568/893; 568/890; 568/891; 570/223; 570/243; 570/245; 570/254

(58) Field of Classification Search .............. 570/223, 570/243, 245, 254; 568/893, 891, 890
See application file for complete search history.

(56) References Cited

U.S. PATENT DOCUMENTS

| | | | |
|---|---|---|---|
| 2,168,260 | A | 8/1939 | Heisel et al. |
| 2,246,082 | A | 6/1941 | Vaughan et al. |
| 2,488,083 | A | 11/1949 | Gorin et al. |
| 2,677,598 | A | 5/1954 | Crummett et al. |
| 2,941,014 | A | 6/1960 | Rothweiler et al. |
| 3,076,784 | A | 2/1963 | Huermann et al. |
| 3,172,915 | A | 3/1965 | Borkowski et al. |
| 3,246,043 | A | 4/1966 | Rosset et al. |
| 3,273,964 | A | 9/1966 | Rosset |
| 3,294,846 | A | 12/1966 | Livak et al. |
| 3,310,380 | A | 3/1967 | Lester |
| 3,346,340 | A | 10/1967 | Louvar et al. |
| 3,353,916 | A | 11/1967 | Lester |
| 3,353,919 | A | 11/1967 | Stockman |
| 3,496,242 | A | 2/1970 | Berkowitz et al. |
| 3,562,321 | A | 2/1971 | Borkowski et al. |
| 3,598,876 | A | 8/1971 | Bloch |
| 3,657,367 | A | 4/1972 | Blake et al. |
| 3,670,037 | A | 6/1972 | Dugan |
| 3,673,264 | A | 6/1972 | Kuhn |
| 3,679,758 | A | 7/1972 | Schneider |
| 3,702,886 | A | 11/1972 | Argauer et al. |
| 3,705,196 | A | 12/1972 | Turner |
| 3,799,997 | A | 3/1974 | Schmerling |
| 3,865,886 | A | 2/1975 | Schindler et al. |
| 3,876,715 | A | 4/1975 | McNulty et al. |
| 3,879,473 | A | 4/1975 | Stapp |

(Continued)

FOREIGN PATENT DOCUMENTS

| | | |
|---|---|---|
| BR | 0210054 | 8/2004 |
| CA | 1099656 | 4/1981 |

(Continued)

OTHER PUBLICATIONS

U.S. Appl. No. 60/487,364, filed Jul. 15, 2003, Lorkovic et al.
U.S. Appl. No. 60/559,844, filed Apr. 6, 2004, Sherman et al.
U.S. Appl. No. 60/765,115, filed Feb. 3, 2006, Gadewar et al.
Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP2007061594, Method for decomposing organohalogen compound and mobile decomposition system, Publication date: Mar. 15, 2007, Inventor: Koichi et al., esp@cenet database—worldwide.

(Continued)

*Primary Examiner* — Elvis O Price
(74) *Attorney, Agent, or Firm* — Adolph Locklar

(57) ABSTRACT

Improvements in previously disclosed methods of and apparatuses for converting alkanes, alkenes, and aromatics to olefins, alcohols, ethers, and aldehydes includes: safety improvements, use of alternative feedstocks, process simplification, improvements to the halogenation step, improvements to the reproportionation step, improvements to the solid oxide reaction, improvements to solid oxide regeneration, improvements in separations, maintenance, start-up, shut-down, and materials of construction.

20 Claims, No Drawings

U.S. PATENT DOCUMENTS

| | | |
|---|---|---|
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,194,990 A | 3/1980 | Pieters et al. |
| 4,197,420 A | 4/1980 | Ferraris et al. |
| 4,219,680 A | 8/1980 | Konig et al. |
| 4,249,031 A | 2/1981 | Drent et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,735,747 A | 4/1988 | Ollivier et al. |
| 4,737,594 A | 4/1988 | Olah |
| 4,748,013 A | 5/1988 | Saito et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barm |

| | | | | | | |
|---|---|---|---|---|---|---|
| 4,795,737 | A | 1/1989 | Rule et al. | 5,157,189 | A | 10/1992 | Karra |
| 4,795,843 | A | 1/1989 | Imai et al. | 5,160,502 | A | 11/1992 | Kimble et al. |
| 4,795,848 | A | 1/1989 | Teller et al. | 5,166,452 | A | 11/1992 | Gradl et al. |
| 4,804,797 | A | 2/1989 | Minet et al. | 5,175,382 | A | 12/1992 | Hebgen et al. |
| 4,804,800 | A | 2/1989 | Bortinger et al. | 5,178,748 | A | 1/1993 | Casci et al. |
| 4,808,763 | A | 2/1989 | Shum | 5,185,479 | A | 2/1993 | Stauffer |
| 4,814,527 | A | 3/1989 | Diesen | 5,188,725 | A | 2/1993 | Harandi |
| 4,814,532 | A | 3/1989 | Yoshida et al. | 5,191,142 | A | 3/1993 | Marshall et al. |
| 4,814,535 | A | 3/1989 | Yurchak | 5,194,244 | A | 3/1993 | Brownscombe et al. |
| 4,814,536 | A | 3/1989 | Yurchak | 5,202,506 | A | 4/1993 | Kirchner et al. |
| 4,849,562 | A | 7/1989 | Buhs et al. | 5,202,511 | A | 4/1993 | Salinas, III et al. |
| 4,849,573 | A | 7/1989 | Kaefing | 5,210,357 | A | 5/1993 | Kolts et al. |
| 4,851,602 | A | 7/1989 | Harandi et al. | 5,215,648 | A | 6/1993 | Zones et al. |
| 4,851,606 | A | 7/1989 | Ragonese et al. | 5,223,471 | A | 6/1993 | Washecheck |
| 4,886,925 | A | 12/1989 | Harandi | 5,228,888 | A | 7/1993 | Gmelin et al. |
| 4,886,932 | A | 12/1989 | Leyshon | 5,233,113 | A | 8/1993 | Periana et al. |
| 4,891,463 | A | 1/1990 | Chu | 5,237,115 | A | 8/1993 | Makovec et al. |
| 4,895,995 | A | 1/1990 | James, Jr. et al. | 5,243,098 | A | 9/1993 | Miller et al. |
| 4,899,000 | A | 2/1990 | Stauffer | 5,243,114 | A | 9/1993 | Johnson et al. |
| 4,899,001 | A | 2/1990 | Kalnes et al. | 5,245,109 | A | 9/1993 | Kaminsky et al. |
| 4,899,002 | A | 2/1990 | Harandi et al. | 5,254,772 | A | 10/1993 | Dukat et al. |
| 4,902,842 | A | 2/1990 | Kalnes et al. | 5,254,790 | A | 10/1993 | Thomas et al. |
| 4,925,995 | A | 5/1990 | Robschlager | 5,264,635 | A | 11/1993 | Le et al. |
| 4,929,781 | A | 5/1990 | James, Jr. et al. | 5,268,518 | A | 12/1993 | West et al. |
| 4,939,310 | A | 7/1990 | Wade | 5,276,226 | A | 1/1994 | Horvath et al. |
| 4,939,311 | A | 7/1990 | Washecheck et al. | 5,276,240 | A | 1/1994 | Timmons et al. |
| 4,945,175 | A | 7/1990 | Hobbs et al. | 5,276,242 | A | 1/1994 | Wu |
| 4,950,811 | A | 8/1990 | Doussain et al. | 5,284,990 | A | 2/1994 | Peterson et al. |
| 4,950,822 | A | 8/1990 | Dileo et al. | 5,300,126 | A | 4/1994 | Brown et al. |
| 4,956,521 | A | 9/1990 | Volles | 5,306,855 | A | 4/1994 | Periana et al. |
| 4,962,252 | A | 10/1990 | Wade | 5,316,995 | A | 5/1994 | Kaminsky et al. |
| 4,973,776 | A | 11/1990 | Allenger et al. | 5,319,132 | A | 6/1994 | Ozawa et al. |
| 4,973,786 | A | 11/1990 | Karra | 5,334,777 | A | 8/1994 | Miller et al. |
| 4,982,024 | A | 1/1991 | Lin et al. | 5,345,021 | A | 9/1994 | Casci et al. |
| 4,982,041 | A | 1/1991 | Campbell | 5,354,916 | A | 10/1994 | Horvath et al. |
| 4,988,660 | A | 1/1991 | Campbell | 5,354,931 | A | 10/1994 | Jan et al. |
| 4,990,696 | A | 2/1991 | Stauffer | 5,366,949 | A | 11/1994 | Schubert |
| 4,990,711 | A | 2/1991 | Chen et al. | 5,371,313 | A | 12/1994 | Ostrowicki |
| 5,001,293 | A | 3/1991 | Nubel et al. | 5,382,704 | A | 1/1995 | Krespan et al. |
| 5,004,847 | A | 4/1991 | Beaver et al. | 5,382,743 | A | 1/1995 | Beech, Jr. et al. |
| 5,013,424 | A | 5/1991 | James, Jr. et al. | 5,382,744 | A | 1/1995 | Abbott et al. |
| 5,013,793 | A | 5/1991 | Wang et al. | 5,385,718 | A | 1/1995 | Casci et al. |
| 5,019,652 | A | 5/1991 | Taylor et al. | 5,395,981 | A | 3/1995 | Marker |
| 5,026,934 | A | 6/1991 | Bains et al. | 5,399,258 | A | 3/1995 | Fletcher et al. |
| 5,026,937 | A | 6/1991 | Bricker | 5,401,890 | A | 3/1995 | Parks |
| 5,026,944 | A | 6/1991 | Allenger et al. | 5,401,894 | A | 3/1995 | Brasier et al. |
| 5,034,566 | A | 7/1991 | Ishino et al. | 5,406,017 | A | 4/1995 | Withers, Jr. |
| 5,043,502 | A | 8/1991 | Martindale et al. | 5,414,173 | A | 5/1995 | Garces et al. |
| 5,055,235 | A | 10/1991 | Brackenridge et al. | 5,430,210 | A | 7/1995 | Grasselli et al. |
| 5,055,633 | A | 10/1991 | Volles | 5,430,214 | A | 7/1995 | Smith et al. |
| 5,055,634 | A | 10/1991 | Volles | 5,430,219 | A | 7/1995 | Sanfilippo et al. |
| 5,059,744 | A | 10/1991 | Harandi et al. | 5,436,378 | A | 7/1995 | Masini et al. |
| 5,068,478 | A | 11/1991 | Miller et al. | 5,444,168 | A | 8/1995 | Brown |
| 5,071,449 | A | 12/1991 | Sircar | 5,446,234 | A | 8/1995 | Casci et al. |
| 5,071,815 | A | 12/1991 | Wallace | 5,453,557 | A | 9/1995 | Harley et al. |
| 5,073,656 | A | 12/1991 | Chafin et al. | 5,456,822 | A | 10/1995 | Marcilly et al. |
| 5,073,657 | A | 12/1991 | Warren | 5,457,255 | A | 10/1995 | Kumata et al. |
| 5,082,473 | A | 1/1992 | Keefer | 5,464,799 | A | 11/1995 | Casci et al. |
| 5,082,816 | A | 1/1992 | Teller et al. | 5,465,699 | A | 11/1995 | Voigt |
| 5,085,674 | A | 2/1992 | Leavitt | 5,470,377 | A | 11/1995 | Whitlock |
| 5,087,779 | A | 2/1992 | Nubel et al. | 5,480,629 | A | 1/1996 | Thompson et al. |
| 5,087,786 | A | 2/1992 | Nubel et al. | 5,486,627 | A | 1/1996 | Quarderer et al. |
| 5,087,787 | A | 2/1992 | Kimble et al. | 5,489,719 | A | 2/1996 | Le et al. |
| 5,093,542 | A | 3/1992 | Gaffney | 5,489,727 | A | 2/1996 | Randolph et al. |
| 5,096,469 | A | 3/1992 | Keefer | 5,500,297 | A | 3/1996 | Thompson et al. |
| 5,097,083 | A | 3/1992 | Stauffer | 5,510,525 | A | 4/1996 | Sen et al. |
| 5,099,084 | A | 3/1992 | Stauffer | 5,523,503 | A | 6/1996 | Funk et al. |
| 5,105,045 | A | 4/1992 | Kimble et al. | 5,525,230 | A | 6/1996 | Wrigley et al. |
| 5,105,046 | A | 4/1992 | Washecheck | 5,538,540 | A | 7/1996 | Whitlock |
| 5,107,032 | A | 4/1992 | Erb et al. | 5,563,313 | A | 10/1996 | Chung et al. |
| 5,107,051 | A | 4/1992 | Pannell | 5,565,092 | A | 10/1996 | Pannell et al. |
| 5,107,061 | A | 4/1992 | Ou et al. | 5,565,616 | A | 10/1996 | Li et al. |
| 5,108,579 | A | 4/1992 | Casci | 5,571,762 | A | 11/1996 | Clerici et al. |
| 5,118,899 | A | 6/1992 | Kimble et al. | 5,571,885 | A | 11/1996 | Chung et al. |
| 5,120,332 | A | 6/1992 | Wells | 5,599,381 | A | 2/1997 | Whitlock |
| 5,132,343 | A | 7/1992 | Zwecker et al. | 5,600,043 | A | 2/1997 | Johnston et al. |
| 5,138,112 | A | 8/1992 | Gosling et al. | 5,600,045 | A | 2/1997 | Van Der Aalst et al. |
| 5,139,991 | A | 8/1992 | Taylor et al. | 5,609,654 | A | 3/1997 | Le et al. |
| 5,146,027 | A | 9/1992 | Gaffney | 5,633,419 | A | 5/1997 | Spencer et al. |

| | | | | | | |
|---|---|---|---|---|---|---|
| 5,639,930 | A | 6/1997 | Penick | 6,320,085 | B1 | 11/2001 | Arvai et al. |
| 5,653,956 | A | 8/1997 | Zones | 6,337,063 | B1 | 1/2002 | Rouleau et al. |
| 5,656,149 | A | 8/1997 | Zones et al. | 6,342,200 | B1 | 1/2002 | Rouleau et al. |
| 5,661,097 | A | 8/1997 | Spencer et al. | 6,368,490 | B1 | 4/2002 | Gestermann |
| 5,663,465 | A | 9/1997 | Clegg et al. | 6,369,283 | B1 | 4/2002 | Guram et al. |
| 5,663,474 | A | 9/1997 | Pham et al. | 6,372,949 | B1 | 4/2002 | Brown et al. |
| 5,675,046 | A | 10/1997 | Ohno et al. | 6,376,731 | B1 | 4/2002 | Evans et al. |
| 5,675,052 | A | 10/1997 | Menon et al. | 6,380,328 | B1 | 4/2002 | McConville et al. |
| 5,679,134 | A | 10/1997 | Brugerolle et al. | 6,380,423 | B2 | 4/2002 | Banning et al. |
| 5,679,879 | A | 10/1997 | Mercier et al. | 6,380,444 | B1 | 4/2002 | Bjerrum et al. |
| 5,684,213 | A | 11/1997 | Nemphos et al. | 6,395,945 | B1 | 5/2002 | Randolph |
| 5,693,191 | A | 12/1997 | Pividal et al. | 6,403,840 | B1 | 6/2002 | Zhou et al. |
| 5,695,890 | A | 12/1997 | Thompson et al. | 6,406,523 | B1 | 6/2002 | Connor et al. |
| 5,698,747 | A | 12/1997 | Godwin et al. | 6,423,211 | B1 | 7/2002 | Randolph et al. |
| 5,705,712 | A | 1/1998 | Frey et al. | 6,426,441 | B1 | 7/2002 | Randolph et al. |
| 5,705,728 | A | 1/1998 | Viswanathan et al. | 6,426,442 | B1 | 7/2002 | Ichikawa et al. |
| 5,705,729 | A | 1/1998 | Huang | 6,452,058 | B1 * | 9/2002 | Schweizer et al. ............ 570/223 |
| 5,708,246 | A | 1/1998 | Camaioni et al. | 6,455,650 | B1 | 9/2002 | Lipian et al. |
| 5,720,858 | A | 2/1998 | Noceti et al. | 6,462,243 | B1 | 10/2002 | Zhou et al. |
| 5,728,897 | A | 3/1998 | Buysch et al. | 6,465,699 | B1 | 10/2002 | Grosso |
| 5,728,905 | A | 3/1998 | Clegg et al. | 6,465,969 | B1 | 10/2002 | Zhou et al. |
| 5,734,073 | A | 3/1998 | Chambers et al. | 6,472,345 | B2 | 10/2002 | Hintermann et al. |
| 5,741,949 | A | 4/1998 | Mack | 6,472,572 | B1 | 10/2002 | Zhou et al. |
| 5,744,669 | A | 4/1998 | Kalnes et al. | 6,475,463 | B1 | 11/2002 | Elomari et al. |
| 5,750,801 | A | 5/1998 | Buysch et al. | 6,475,464 | B1 | 11/2002 | Rouleau et al. |
| 5,770,175 | A | 6/1998 | Zones | 6,479,705 | B2 | 11/2002 | Murata et al. |
| 5,776,871 | A | 7/1998 | Cothran et al. | 6,482,997 | B2 | 11/2002 | Petit-Clair et al. |
| 5,780,703 | A | 7/1998 | Chang et al. | 6,486,368 | B1 | 11/2002 | Zhou et al. |
| 5,798,314 | A | 8/1998 | Spencer et al. | 6,495,484 | B1 | 12/2002 | Holtcamp |
| 5,814,715 | A | 9/1998 | Chen et al. | 6,509,485 | B1 | 1/2003 | Mul et al. |
| 5,817,904 | A | 10/1998 | Vic et al. | 6,511,526 | B2 | 1/2003 | Jagger et al. |
| 5,821,394 | A | 10/1998 | Schoebrechts et al. | 6,514,319 | B2 | 2/2003 | Keefer et al. |
| 5,847,224 | A | 12/1998 | Koga et al. | 6,518,474 | B1 | 2/2003 | Sanderson et al. |
| 5,849,978 | A | 12/1998 | Benazzi et al. | 6,518,476 | B1 | 2/2003 | Culp et al. |
| 5,866,735 | A | 2/1999 | Cheung et al. | 6,525,228 | B2 | 2/2003 | Chauvin et al. |
| 5,895,831 | A | 4/1999 | Brasier et al. | 6,525,230 | B2 | 2/2003 | Grosso |
| 5,898,086 | A | 4/1999 | Harris | 6,528,693 | B1 | 3/2003 | Gandy et al. |
| 5,905,169 | A | 5/1999 | Jacobson | 6,538,162 | B2 | 3/2003 | Chang et al. |
| 5,906,892 | A | 5/1999 | Thompson et al. | 6,540,905 | B1 | 4/2003 | Elomari |
| 5,908,963 | A | 6/1999 | Voss et al. | 6,545,191 | B1 | 4/2003 | Stauffer |
| 5,952,538 | A | 9/1999 | Vaughn et al. | 6,547,958 | B1 | 4/2003 | Elomari |
| 5,959,170 | A | 9/1999 | Withers | 6,548,040 | B1 | 4/2003 | Rouleau et al. |
| 5,968,236 | A | 10/1999 | Bassine | 6,552,241 | B1 | 4/2003 | Randolph et al. |
| 5,969,195 | A | 10/1999 | Stabel et al. | 6,566,572 | B2 | 5/2003 | Okamoto et al. |
| 5,977,402 | A | 11/1999 | Sekiguchi et al. | 6,572,829 | B2 | 6/2003 | Linkous et al. |
| 5,983,476 | A | 11/1999 | Eshelman et al. | 6,585,953 | B2 | 7/2003 | Roberts et al. |
| 5,986,158 | A | 11/1999 | Van Broekhoven et al. | 6,616,830 | B2 | 9/2003 | Elomari |
| 5,994,604 | A | 11/1999 | Reagen et al. | 6,620,757 | B2 | 9/2003 | McConville et al. |
| 5,998,679 | A | 12/1999 | Miller | 6,632,971 | B2 | 10/2003 | Brown et al. |
| 5,998,686 | A | 12/1999 | Clem et al. | 6,635,793 | B2 | 10/2003 | Mul et al. |
| 6,002,059 | A | 12/1999 | Hellring et al. | 6,641,644 | B2 | 11/2003 | Jagger et al. |
| 6,015,867 | A | 1/2000 | Fushimi et al. | 6,646,102 | B2 | 11/2003 | Boriack et al. |
| 6,018,088 | A | 1/2000 | Olah | 6,669,846 | B2 | 12/2003 | Perriello |
| 6,022,929 | A | 2/2000 | Chen et al. | 6,672,572 | B2 | 1/2004 | Werlen |
| 6,034,288 | A | 3/2000 | Scott et al. | 6,679,986 | B1 | 1/2004 | Da Silva et al. |
| 6,056,804 | A | 5/2000 | Keefer et al. | 6,680,415 | B1 | 1/2004 | Gulotty, Jr. et al. |
| 6,068,679 | A | 5/2000 | Zheng | 6,692,626 | B2 | 2/2004 | Keefer et al. |
| 6,072,091 | A | 6/2000 | Cosyns et al. | 6,692,723 | B2 | 2/2004 | Rouleau et al. |
| 6,087,294 | A | 7/2000 | Klabunde et al. | 6,710,213 | B2 | 3/2004 | Aoki et al. |
| 6,090,312 | A | 7/2000 | Ziaka et al. | 6,713,087 | B2 | 3/2004 | Tracy et al. |
| 6,096,932 | A | 8/2000 | Subramanian | 6,713,655 | B2 | 3/2004 | Yilmaz et al. |
| 6,096,933 | A | 8/2000 | Cheung et al. | RE38,493 | E | 4/2004 | Keefer et al. |
| 6,103,215 | A | 8/2000 | Zones et al. | 6,723,808 | B2 | 4/2004 | Holtcamp |
| 6,107,561 | A | 8/2000 | Thompson | 6,727,400 | B2 | 4/2004 | Messier et al. |
| 6,117,371 | A | 9/2000 | Mack | 6,740,146 | B2 | 5/2004 | Simonds |
| 6,124,514 | A | 9/2000 | Emmrich et al. | 6,753,390 | B2 | 6/2004 | Ehrman et al. |
| 6,127,588 | A | 10/2000 | Kimble et al. | 6,765,120 | B2 | 7/2004 | Weber et al. |
| 6,130,260 | A | 10/2000 | Hall et al. | 6,797,845 | B1 | 9/2004 | Hickman et al. |
| 6,143,939 | A | 11/2000 | Farcasiu et al. | 6,797,851 | B2 | 9/2004 | Martens et al. |
| 6,169,218 | B1 | 1/2001 | Hearn et al. | 6,821,924 | B2 | 11/2004 | Gulotty, Jr. et al. |
| 6,180,841 | B1 | 1/2001 | Fatutto et al. | 6,822,123 | B2 | 11/2004 | Stauffer |
| 6,187,871 | B1 | 2/2001 | Thompson et al. | 6,822,125 | B2 | 11/2004 | Lee et al. |
| 6,187,983 | B1 | 2/2001 | Sun | 6,825,307 | B2 | 11/2004 | Goodall |
| 6,203,712 | B1 | 3/2001 | Bronner et al. | 6,825,383 | B1 | 11/2004 | Dewkar et al. |
| 6,207,864 | B1 | 3/2001 | Henningsen et al. | 6,831,032 | B2 | 12/2004 | Spaether |
| 6,225,517 | B1 | 5/2001 | Nascimento et al. | 6,838,576 | B1 | 1/2005 | Wicki et al. |
| 6,248,218 | B1 | 6/2001 | Linkous et al. | 6,841,063 | B2 | 1/2005 | Elomari |
| 6,265,505 | B1 | 7/2001 | McConville et al. | 6,852,896 | B2 | 2/2005 | Stauffer |
| 6,281,405 | B1 | 8/2001 | Davis et al. | 6,866,950 | B2 | 3/2005 | Connor et al. |

| | | | | | | |
|---|---|---|---|---|---|---|
| 6,869,903 B2 | 3/2005 | Matsunaga | | 7,348,295 B2 | 3/2008 | Zones et al. |
| 6,875,339 B2 | 4/2005 | Rangarajan et al. | | 7,348,464 B2 | 3/2008 | Waycuilis |
| 6,878,853 B2 | 4/2005 | Tanaka et al. | | 7,357,904 B2 | 4/2008 | Zones et al. |
| 6,888,013 B2 | 5/2005 | Paparatto et al. | | 7,361,794 B2 | 4/2008 | Grosso |
| 6,900,363 B2 | 5/2005 | Harth et al. | | 7,390,395 B2 | 6/2008 | Elomari |
| 6,902,602 B2 | 6/2005 | Keefer et al. | | 2002/0102672 A1 | 8/2002 | Mizrahi |
| 6,903,171 B2 | 6/2005 | Rhodes et al. | | 2002/0198416 A1 | 12/2002 | Zhou et al. |
| 6,909,024 B1 | 6/2005 | Jones et al. | | 2003/0004380 A1 | 1/2003 | Grumann |
| 6,921,597 B2 | 7/2005 | Keefer et al. | | 2003/0065239 A1 | 4/2003 | Zhu |
| 6,933,417 B1 | 8/2005 | Henley et al. | | 2003/0069452 A1 | 4/2003 | Sherman et al. |
| 6,946,566 B2 | 9/2005 | Yaegashi et al. | | 2003/0078456 A1 | 4/2003 | Yilmaz et al. |
| 6,953,868 B2 | 10/2005 | Boaen et al. | | 2003/0120121 A1 | 6/2003 | Sherman et al. |
| 6,953,873 B2 | 10/2005 | Cortright et al. | | 2003/0125589 A1 | 7/2003 | Grosso |
| 6,956,140 B2 | 10/2005 | Ehrenfeld | | 2003/0166973 A1 | 9/2003 | Zhou et al. |
| 6,958,306 B2 | 10/2005 | Holtcamp | | 2004/0006246 A1 | 1/2004 | Sherman et al. |
| 6,984,763 B2 | 1/2006 | Schweizer et al. | | 2004/0062705 A1 | 4/2004 | Leduc |
| 7,001,872 B2 | 2/2006 | Pyecroft et al. | | 2004/0152929 A1 | 8/2004 | Clarke |
| 7,002,050 B2 | 2/2006 | Santiago Fernandez et al. | | 2004/0158107 A1 | 8/2004 | Aoki |
| 7,011,811 B2 | 3/2006 | Elomari | | 2004/0158108 A1 | 8/2004 | Snoble |
| 7,019,182 B2 | 3/2006 | Grosso | | 2004/0187684 A1 | 9/2004 | Elomari |
| 7,026,145 B2 | 4/2006 | Mizrahi et al. | | 2005/0047927 A1 | 3/2005 | Lee et al. |
| 7,026,519 B2 | 4/2006 | Santiago Fernandez et al. | | 2005/0148805 A1 | 7/2005 | Jones |
| 7,037,358 B2 | 5/2006 | Babicki et al. | | 2005/0171393 A1 | 8/2005 | Lorkovic |
| 7,045,670 B2 | 5/2006 | Johnson et al. | | 2005/0192468 A1 | 9/2005 | Sherman et al. |
| 7,049,388 B2 | 5/2006 | Boriack et al. | | 2005/0215837 A1 | 9/2005 | Hoffpauir |
| 7,053,252 B2 | 5/2006 | Boussand et al. | | 2005/0234276 A1 | 10/2005 | Waycuilis |
| 7,057,081 B2 | 6/2006 | Allison et al. | | 2005/0245772 A1 | 11/2005 | Fong |
| 7,060,865 B2 | 6/2006 | Ding et al. | | 2005/0245777 A1 | 11/2005 | Fong |
| 7,064,238 B2 | 6/2006 | Waycuilis | | 2005/0267224 A1 | 12/2005 | Herling |
| 7,064,240 B2 | 6/2006 | Ohno et al. | | 2006/0025617 A1 | 2/2006 | Begley |
| 7,067,448 B1 | 6/2006 | Weitkamp et al. | | 2006/0100469 A1 | 5/2006 | Waycuilis |
| 7,083,714 B2 | 8/2006 | Elomari | | 2006/0135823 A1 | 6/2006 | Jun |
| 7,084,308 B1 | 8/2006 | Stauffer | | 2006/0138025 A1 | 6/2006 | Zones |
| 7,091,270 B2 | 8/2006 | Zilberman et al. | | 2006/0138026 A1 | 6/2006 | Chen |
| 7,091,387 B2 | 8/2006 | Fong et al. | | 2006/0149116 A1 | 7/2006 | Slaugh |
| 7,091,391 B2 | 8/2006 | Stauffer | | 2006/0229228 A1 | 10/2006 | Komon et al. |
| 7,094,936 B1 | 8/2006 | Owens et al. | | 2006/0229475 A1 | 10/2006 | Weiss et al. |
| 7,098,371 B2 | 8/2006 | Mack et al. | | 2006/0270863 A1 | 11/2006 | Reiling |
| 7,105,710 B2 | 9/2006 | Boons et al. | | 2006/0288690 A1 | 12/2006 | Elomari |
| 7,138,534 B2 | 11/2006 | Forlin et al. | | 2007/0004955 A1 | 1/2007 | Kay |
| 7,141,708 B2 | 11/2006 | Marsella et al. | | 2007/0078285 A1 | 4/2007 | Dagle |
| 7,145,045 B2 | 12/2006 | Harmsen et al. | | 2007/0100189 A1 | 5/2007 | Stauffer |
| 7,148,356 B2 | 12/2006 | Smith, III et al. | | 2007/0129584 A1 | 6/2007 | Basset |
| 7,148,390 B2 | 12/2006 | Zhou et al. | | 2007/0142680 A1 | 6/2007 | Ayoub |
| 7,151,199 B2 | 12/2006 | Martens et al. | | 2007/0148067 A1 | 6/2007 | Zones |
| 7,161,050 B2 | 1/2007 | Sherman et al. | | 2007/0148086 A1 | 6/2007 | Zones |
| 7,169,730 B2 | 1/2007 | Ma et al. | | 2007/0149778 A1 | 6/2007 | Zones |
| 7,176,340 B2 | 2/2007 | Van Broekhoven et al. | | 2007/0149789 A1 | 6/2007 | Zones |
| 7,176,342 B2 | 2/2007 | Bellussi et al. | | 2007/0149819 A1 | 6/2007 | Zones |
| 7,182,871 B2 | 2/2007 | Perriello | | 2007/0149824 A1 | 6/2007 | Zones |
| 7,193,093 B2 | 3/2007 | Murray et al. | | 2007/0149837 A1 | 6/2007 | Zones |
| 7,196,239 B2 | 3/2007 | Van Egmond et al. | | 2007/0197801 A1 | 8/2007 | Bolk |
| 7,199,083 B2 | 4/2007 | Zevallos | | 2007/0197847 A1 | 8/2007 | Liu |
| 7,199,255 B2 | 4/2007 | Murray et al. | | 2007/0213545 A1 | 9/2007 | Bolk |
| 7,208,641 B2 | 4/2007 | Nagasaki et al. | | 2007/0238905 A1 | 10/2007 | Arredondo |
| 7,214,750 B2 | 5/2007 | McDonald et al. | | 2007/0238909 A1 | 10/2007 | Gadewar et al. |
| 7,220,391 B1 | 5/2007 | Huang et al. | | 2007/0251382 A1 | 11/2007 | Gadewar |
| 7,226,569 B2 | 6/2007 | Elomari | | 2007/0276168 A1 | 11/2007 | Garel |
| 7,226,576 B2 | 6/2007 | Elomari | | 2007/0284284 A1 | 12/2007 | Zones |
| 7,230,150 B2 | 6/2007 | Grosso et al. | | 2008/0171898 A1 | 7/2008 | Waycuilis |
| 7,230,151 B2 | 6/2007 | Martens et al. | | 2008/0183022 A1 | 7/2008 | Waycuilis |
| 7,232,872 B2 | 6/2007 | Shaffer et al. | | 2008/0188697 A1 | 8/2008 | Lorkovic |
| 7,238,846 B2 | 7/2007 | Janssen et al. | | 2008/0269534 A1 | 10/2008 | Lorkovic |
| 7,244,795 B2 | 7/2007 | Agapiou et al. | | 2008/0314758 A1 | 12/2008 | Grosso |
| 7,244,867 B2 | 7/2007 | Waycuilis | | 2009/0069606 A1 | 3/2009 | Komon |
| 7,250,107 B2 | 7/2007 | Benazzi et al. | | 2009/0127156 A1 | 5/2009 | Tung |
| 7,250,542 B2 | 7/2007 | Smith, Jr. et al. | | 2010/0096588 A1 | 4/2010 | Gadewar |
| 7,252,920 B2 | 8/2007 | Kurokawa et al. | | 2010/0099928 A1 | 4/2010 | Gadewar |
| 7,253,327 B2 | 8/2007 | Janssens et al. | | 2010/0099929 A1 | 4/2010 | Gadewar |
| 7,253,328 B2 | 8/2007 | Stauffer | | 2010/0099930 A1 | 4/2010 | Stoimenov |
| 7,265,193 B2 | 9/2007 | Weng et al. | | 2010/0105972 A1 | 4/2010 | Lorkovic |
| 7,267,758 B2 | 9/2007 | Benazzi et al. | | 2010/0121119 A1 | 5/2010 | Sherman |
| 7,268,263 B1 | 9/2007 | Frey et al. | | | | |
| 7,271,303 B1 | 9/2007 | Sechrist et al. | | FOREIGN PATENT DOCUMENTS | | |
| 7,273,957 B2 | 9/2007 | Bakshi et al. | | CA | 1101441 | 5/1981 |
| 7,282,603 B2 | 10/2007 | Richards | | CA | 1202610 | 4/1986 |
| 7,285,698 B2 | 10/2007 | Liu et al. | | CA | 2447761 A1 | 11/2002 |
| 7,304,193 B1 | 12/2007 | Frey et al. | | CA | 2471295 A1 | 7/2003 |
| 7,342,144 B2 | 3/2008 | Kaizik et al. | | CA | 2542857 | 5/2005 |

| | | | | | | |
|---|---|---|---|---|---|---|
| CA | 2236126 | 8/2006 | | WO | 01/14300 A1 | 3/2001 |
| CA | 2203115 | 9/2006 | | WO | 01/38275 A1 | 5/2001 |
| CA | 2510093 | 12/2006 | | WO | 01/44149 A1 | 6/2001 |
| EP | 0021497 | 1/1981 | | WO | 02/094749 A1 | 11/2002 |
| EP | 0164798 A1 | 12/1985 | | WO | 02/094750 A1 | 11/2002 |
| EP | 0418971 A1 | 3/1991 | | WO | 02/094751 A2 | 11/2002 |
| EP | 0418974 A1 | 3/1991 | | WO | 02/094752 A1 | 11/2002 |
| EP | 0418975 A1 | 3/1991 | | WO | 03/000635 A1 | 1/2003 |
| EP | 0510238 A1 | 10/1992 | | WO | 03/002251 A2 | 1/2003 |
| EP | 0526908 A2 | 2/1993 | | WO | 03/018524 A1 | 3/2003 |
| EP | 0346612 B1 | 8/1993 | | WO | 03/020676 A1 | 3/2003 |
| EP | 0560546 A1 | 9/1993 | | WO | 03/022827 A1 | 3/2003 |
| EP | 0976705 A1 | 7/1998 | | WO | 03/043575 A2 | 5/2003 |
| EP | 1186591 A2 | 3/2002 | | WO | 03/051813 A1 | 6/2003 |
| EP | 1253126 A1 | 10/2002 | | WO | 03/062143 A1 | 7/2003 |
| EP | 1312411 A2 | 5/2003 | | WO | 03/062172 A1 | 7/2003 |
| EP | 1395536 | 3/2004 | | WO | 03/078366 A1 | 9/2003 |
| EP | 1404636 | 4/2004 | | WO | 2004/018093 A2 | 3/2004 |
| EP | 1235769 B1 | 5/2004 | | WO | 2004/067487 A2 | 8/2004 |
| EP | 1435349 A2 | 7/2004 | | WO | 2005/014168 A1 | 2/2005 |
| EP | 1440939 A1 | 7/2004 | | WO | 2005/019143 A1 | 3/2005 |
| EP | 1474371 | 11/2004 | | WO | 2005/021468 A1 | 3/2005 |
| EP | 1235772 B1 | 1/2005 | | WO | 2005/035121 A2 | 4/2005 |
| EP | 1661620 A1 | 5/2006 | | WO | 2005/037758 A1 | 4/2005 |
| EP | 1760057 A1 | 3/2007 | | WO | 2005/054120 A1 | 6/2005 |
| EP | 1689728 B1 | 4/2007 | | WO | 2005/056525 A2 | 6/2005 |
| EP | 1808227 A1 | 7/2007 | | WO | 2005/058782 A1 | 6/2005 |
| EP | 1837320 A1 | 9/2007 | | WO | 2005/090272 A1 | 9/2005 |
| GB | 5125 | 0/1912 | | WO | 2005/095310 A2 | 10/2005 |
| GB | 156122 | 3/1922 | | WO | 2005/105709 A1 | 11/2005 |
| GB | 294100 | 6/1929 | | WO | 2005/105715 A1 | 11/2005 |
| GB | 363009 | 12/1931 | | WO | 2005/110953 A1 | 11/2005 |
| GB | 402928 | 12/1933 | | WO | 2005/113437 A1 | 12/2005 |
| GB | 474922 A | 11/1937 | | WO | 2005/113440 A1 | 12/2005 |
| GB | 536491 | 5/1941 | | WO | 2006/007093 A1 | 1/2006 |
| GB | 553950 | 6/1943 | | WO | 2006/015824 A1 | 2/2006 |
| GB | 586483 | 3/1947 | | WO | 2006/019399 A2 | 2/2006 |
| GB | 775590 | 5/1957 | | WO | 2006/020234 A1 | 2/2006 |
| GB | 793214 | 4/1958 | | WO | 2006/036293 A1 | 4/2006 |
| GB | 796048 | 6/1958 | | WO | 2006/039213 A1 | 4/2006 |
| GB | 796085 | 6/1958 | | WO | 2006/039354 A2 | 4/2006 |
| GB | 883256 | 11/1961 | | WO | 2006/043075 A1 | 4/2006 |
| GB | 950975 | 3/1964 | | WO | 2006/053345 A1 | 5/2006 |
| GB | 950976 | 3/1964 | | WO | 2006-067155 A2 | 6/2006 |
| GB | 991303 | 5/1965 | | WO | 2006/067188 A1 | 6/2006 |
| GB | 995960 | 6/1965 | | WO | 2006/067190 A1 | 6/2006 |
| GB | 1015033 | 12/1965 | | WO | 2006/067191 A1 | 6/2006 |
| GB | 1104294 | 2/1968 | | WO | 2006/067192 A1 | 6/2006 |
| GB | 1133752 | 11/1968 | | WO | 2006/067193 A1 | 6/2006 |
| GB | 1172002 | 11/1969 | | WO | 2006/069107 A2 | 6/2006 |
| GB | 1212240 | 11/1970 | | WO | 2006/071354 A1 | 7/2006 |
| GB | 1233299 | 5/1971 | | WO | 2006/076942 A1 | 7/2006 |
| GB | 1253618 | 11/1971 | | WO | 2006/083427 A1 | 8/2006 |
| GB | 1263806 A | 2/1972 | | WO | 2006-100312 A2 | 9/2006 |
| GB | 1446803 | 8/1976 | | WO | 2006/104909 A2 | 10/2006 |
| GB | 1542112 | 3/1979 | | WO | 2006/104914 A1 | 10/2006 |
| GB | 2095243 A | 9/1982 | | WO | 2006/111997 A1 | 10/2006 |
| GB | 2095245 A | 9/1982 | | WO | 2006/113205 A2 | 10/2006 |
| GB | 2095249 A | 9/1982 | | WO | 2006/118935 A2 | 11/2006 |
| GB | 2116546 A | 9/1982 | | WO | 2007/001934 A2 | 1/2007 |
| GB | 2120249 A | 11/1983 | | WO | 2007/017900 A2 | 2/2007 |
| GB | 2185754 A | 7/1987 | | WO | 2007/044139 A1 | 4/2007 |
| GB | 2191214 A | 12/1987 | | WO | 2007/046986 A2 | 4/2007 |
| JP | 2004-529189 | 9/2004 | | WO | 2007/050745 A1 | 5/2007 |
| WO | 83/00859 | 3/1983 | | WO | 2007/071046 A1 | 6/2007 |
| WO | 85/04863 | 11/1985 | | WO | 2007/079038 A2 | 7/2007 |
| WO | 90/08120 | 7/1990 | | WO | 2007/091009 A1 | 8/2007 |
| WO | 90/08752 | 8/1990 | | WO | 2007/094995 A2 | 8/2007 |
| WO | 91/18856 | 12/1991 | | WO | 2007/107031 A1 | 9/2007 |
| WO | 92/03401 | 3/1992 | | WO | 2007/111997 A2 | 10/2007 |
| WO | 92/12946 | 8/1992 | | WO | 2007/114479 A1 | 10/2007 |
| WO | 93/16798 | 9/1993 | | WO | 2007/125332 A1 | 11/2007 |
| WO | 85/04867 | 11/1995 | | WO | 2007/130054 A1 | 11/2007 |
| WO | 96/22263 | 7/1996 | | WO | 2007/130055 A1 | 11/2007 |
| WO | 97/44302 | 11/1997 | | WO | 2007/141295 A1 | 12/2007 |
| WO | 98/12165 | 3/1998 | | WO | 2007/142745 A1 | 12/2007 |
| WO | 99/07443 | 2/1999 | | WO | 2008/036562 | 3/2008 |
| WO | 00/07718 A1 | 2/2000 | | WO | 2008/036563 | 3/2008 |
| WO | 00/09261 A1 | 2/2000 | | WO | 2008/106319 | 9/2008 |

| | | |
|---|---|---|
| WO | 2008/157043 | 12/2008 |
| WO | 2008/157044 | 12/2008 |
| WO | 2008/157045 | 12/2008 |
| WO | 2008/157046 | 12/2008 |
| WO | 2008/157047 | 12/2008 |

OTHER PUBLICATIONS

Abstract of JP2007099729, Method for producing alpha-methylstyrene or cumene, Publication date: Apr. 19, 2007, Inventor: Toshio, esp@cenet database—worldwide.

Abstract of RO119778, Process for preparing perchloroethylene, Publication date: Mar. 30, 2005, Inventor: Horia et al., esp@cenet database—worldwide.

Abstract of WO0105737, Method for preparing a carboxylic acid, Publication date: Jan. 25, 2001, Inventor: Pascal et al., esp@cenet database—worldwide.

Abstract of WO0105738, Method for preparing a carboxylic acid, Publication date: Jan. 25, 2001, Inventor: Pascal et al., esp@cenet database—worldwide.

Abstract of WO2004092099, Method for producing cyclic enols, Publication date: Oct. 28, 2004, Inventor: Marko et al., esp@cenet database—worldwide.

Abstract of WO2006063852, Electroluminescent polymers and use thereof, Publication date: Jun. 22, 2006, Inventor: Arne et al., esp@cenet database—worldwide.

Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.

Abstract of WO2007028761, Method for chlorinating alcohols, Publication date: Mar. 15, 2007, Inventor: Rohde et al., esp@cenet database—worldwide.

Abstract of WO2007128842, Catalytic transalkylation of dialkyl benzenes, Publication date: Nov. 15, 2007, Inventor: Goncalvesalmeida et al., esp@cenet database—worldwide.

Abstract of WO2007137566, Method for catalytic conversion of organic oxygenated compounds from biomaterials, Publication date: Dec. 6, 2007, Inventor: Reschetilowski, esp@cenet database—worldwide.

Abstract of WO9721656, Method for making fluoroalkanols, Publication date: Jun. 19, 1997, Inventor: Gillet, esp@cenet database—worldwide.

Abstract of WO9950213, Method for producing dialkyl ethers, Publication date: Oct. 7, 1999, Inventor: Falkowski Juergen et al., esp@cenet database—worldwide.

Adachi, et al.; Synthesis of Sialyl Lewis X Ganglioside Analogs Containing a Variable Length Spacer Between the Sugar and Lipophilic Moieties; J. Carbohydrate Chem., vol. 17, No. 4-5, (1998), pp. 595-607, XP009081720.

Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.

Abstract of EP0101337, Process for the production of methylene chloride, Publication date: Feb. 22, 1984, Inventor: Olah et al., esp@cenet database—worldwide.

Abstract of EP0407989, Method for the production of 1,1,1-trifluoro-2,2-dichloroethane by photochlorination, Publication date: Jan. 16, 1991, Inventor: Cremer et al., esp@cenet database—worldwide.

Abstract of EP0442258, Process for the preparation of a polyunsaturated olefin, Publication date: Aug. 21, 1991, Inventor. Gaudin et al., esp@cenet database—worldwide.

Abstract of EP0465294, Process for the preparation of unsaturated bromides, Publication date: Jan. 8, 1992, Inventor: Decaudin et al., esp@cenet database—worldwide.

Abstract of EP0549387, Synthesis of n-perfluorooctylbromide, Publication date: Jun. 30, 1993, Inventor: Drivon et al, esp@cenet database—worldwide.

Abstract of EP0850906, Process and apparatus for the etherification of olefinic hydrocarbon feedstocks, Publication date: Jul. 1, 1998, Inventor Masson, esp@cenet database—worldwide.

Abstract of EP0858987, Process for the conversion of lighter alkanes to higher hydrocarbons, Publication date: Aug. 19, 1998, Inventor: Amariglio et al., esp@cenet database—worldwide.

Bakker, et al.; An Exploratory Study of the Addition Reaction of Ethyleneglcol, 2-Chloroethanlo and 1, 3-Dichloro-2-Propanol to 1-Dodecene; J. Am. Oil Chem. Soc., vol. 44, No. 9 (1967), pp. 517-521; XP009081570.

Abstract of EP0235110, Process for the stabilization of silicalite catalysts, Publication date: Sep. 2, 1987, Inventor: Debras et al., esp@cenet database—worldwide.

Bouzide et al.; Highly Selective Silver (I) Oxide Mediated Monoprotection of Symmetricl Diols; Tetrahedron Letters, Elsevier, vol. 38, No. 34 (1997), pp. 5945-5948; XP004094157.

Combined International Search Report and Written Opinion Dated Apr. 17, 2007 for PCT/US06/13394, in the name of GRT, Inc.

Gibson; Phase-Transfer Synthesis of Monoalkyl Ethers of Oligoethylene Glycols; Journal of Organic Chemistry, vol. 45, No. 6 (1980) pp. 1095-1098; XP002427776.

Klabunde, Kenneth J., et al., Changes in Texture and Catalytic Activity of Nanocrystalline MgO during Its Transformation to MgC12 in the Reaction with 1-Chlorobutane, J. Phys. Chem. B 2001, 105, 3937-3941.

Loiseau et al.; Multigram Synthesis of Well-Defined Extended Bifunctional Polyethylene Glycol (PEG) Chains; J. of Organic Chem., vol. 69, No. 3 (2004), pp. 639-647; XP002345040.

Mihai et al.; Application of Bronsted-type LFER in the study of phospholipase C mechanism; J. Am. Chem. Soc., vol. 125, No. 11 (2003) pp. 3236-3242; XP002427799.

Motupally et al., Recycling Chlorine from Hydrogen Chloride: A New and Economical Electrolytic Process, The Electrochemical Society Interface, Fall 1998.

Nishikawa et al.; Ultrasonic Relaxations in Aqueous Solutions of Alcohols and the Balance Between Hydrophobicity and Hydrophilicity of the Solutes; J. Phys. Chem. vol. 97, No. 14 (1993), pp. 3539-3544; XP002427775.

Prelog et al.; Chirale 2,2'-Polyoxaalkano-9,9'-Spirobifluorene; Helvetica Chimica ACTA, vol. 62, No. 7, (1979) pp. 2285-2302; XP002030901.

Shimizu et al., Gas-Phase Electrolysis of Hydrobromic Acid Using PTFE-Bonded Carbon Eletrode, Int. J. Hydrogen Energy, vol. 13, No. 6. pp. 345-349, 1988.

Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.

Whitesides et al.; Nuclear Magnetic Resonance Spectroscopy. The Effect of Structure on Magnetic Nonequivalence Due to Molecular Asymmetry; J. Am. Chem. Soc., vol. 86, No. 13 (1964), pp. 2628-2634; XP002427774.

JLM Technology Ltd.; "The Miller GLS Technology for Conversion of Light Hydrocarbons to Alcohols" New Science for the Benefit of Humanity; May 31, 2000; pp. 1-10.

Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.

Taylor, Charles E.; "Conversion of Substituted Methanes Over ZSM-Catalysts"; 2000; pp. 3633-3638; Studies in Surface Science and Catalysis 130; Elsevier Science B.V.

ZSM-5 Catalyst; http://chemelab.ucsd.edu/methanol/memos/ZSM-5.html; Nov. 6, 2003; p. 1.

Final Report; "Abstract"; http://chemelab.ucsd.edu/methanol/memos/final.html; May 9, 2004; pp. 1-7.

Driscoll, Daniel J.; "Direct Methane Conversion"; Federal Energy Technology Center, U.S. Department of Energy; M970779; 2001; pp. 1-10.

Olah et al.; "Selective Monohalogenation of Methane over Supported Acid or Platinum Metal Catalysts and Hydrolysis of Methyl Halides . . . "; J. American Chemical Society 1985, vol. 107; 0002-7863/85/1507-7097$01.50/0; pp. 7097-7105.

Murray et al.; "Conversion of Methyl Halides to Hydrocarbons on Basic Zeolites: A Discovery by in Situ NMR"; J. American Chemical Society 1993, vol. 115; pp. 4732-4741.

Lorkovic et al.; "A Novel Integrated Process for the Functionalization of Methane and Ethane: Bromine as Mediator", Catalysis Today 98; 2004; pp. 317-322.

Lorkovic et al.; "C1 Oxidative Coupling via Bromine Activation and Tandem Catalytic Condensation over CaO/Zeolite Composites II . . . "; Catalysis Today 98; 2004; pp. 589-594.

Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.

Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.

Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.

Zhou, Xiao-Ping et al.; "An Integrated Process for Partial Oxidation of Alkanes"; Chem. Commun. 2003; The Royal Society of Chemistry 2003; pp. 2294-2295.

Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesoporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isao et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST Chemistry WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

Abstract of BE812868, Aromatic hydrocarbons prodn. from chlorinated hydrocarbons, Publication date: Sep. 27, 1974, esp@cenet database—worldwide.

Abstract of BE814900, Volatile aramatic cpds. prodn., Publication date: Sep. 2, 1974, esp@cenet database—worldwide.

Abstract of CN1199039, Pentanol and its production process, Publication date: Nov. 18, 1998, Inventor: Kailun, esp@cenet database—worldwide.

Abstract of CN1210847, Process for producing low carbon alcohol by directly hydrating low carbon olefines, Publication date: Mar. 17, 1999, Inventor: Zhenguo et al., esp@cenet database—worldwide.

Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.

Abstract of CN1623969, Method for preparing 1, 4-benzene dimethanol, Publication date: Jun. 8, 2005, Inventor: Jiarong et al., esp@cenet database—worldwide.

Abstract of CN1657592, Method for converting oil to multiple energy fuel product, Publication date: Aug. 24, 2005, Inventor: Li, esp@cenet database—worldwide.

Abstract of CN1687316, Method for producing biologic diesel oil from rosin, Publication date: Oct. 26, 2005, Inventor: Jianchun et al., esp@cenet database—worldwide.

Abstract of CN1696248, Method for synthesizing biologic diesel oil based on ion liquid, Publication date: Nov. 16, 2005, Inventor: Sun, esp@cenet database—worldwide.

Abstract of CN1699515, Process for preparing bio-diesel-oil by using microalgae fat, Publication date: Nov. 23, 2005, Inventor: Miao, esp@cenet database—worldwide.

Abstract of CN1704392, Process for producing alkylbenzene, Publication date: Dec. 7, 2005, Inventor: Gao, esp@cenet database—worldwide.

Abstract of CN1724612, Biological diesel oil catalyst and method of synthesizing biological diesel oil using sai catalyst, Publication date: Jan. 25, 2006, Inventor: Gu, esp@cenet database—worldwide.

Abstract of CN1986737, Process of producing biodiesel oil with catering waste oil, Publication date: Jun. 27, 2007, Inventor: Chen, esp@cenet database—worldwide.

Abstract of CN100999680, Esterification reaction tech. of preparing biodiesel by waste oil, Publication date: Jul. 18, 2007, Inventor: Weiming, esp@cenet database—worldwide.

Abstract of CN101016229, Refining method for bromomeoamyl alcohol, Publication date: Aug. 15, 2007, Inventor: Tian, esp@cenet database—worldwide.

Abstract of DE3209964, Process for the preparation of chlorinated hydrocarbons, Publication date: Nov. 11, 1982, Inventor: Pyke et al., esp@cenet database—worldwide.

Abstract of DE3210196, Process for the preparation of a monochlorinated olefin, Publication date: Jan. 5, 1983, Inventor: Pyke et al., esp@cenet database—worldwide.

Abstract of DE3226028, Process for the preparation of monochlorinated olefin, Publication date: Feb. 3, 1983, Inventor: Pyke et al., esp@cenet database—worldwide.

Abstract of DE3334225, Process for the preparation of 1, 2-dichloroethane, Publication date: Apr. 4, 1985, Inventor: Hebgen et al., esp@cenet database—worldwide.

Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.

Abstract of DE4434823, Continuous prodn. of hydroxy-benzyl alkyl ether, Publication date: Apr. 4, 1996, Inventor Stein et al., esp@cenet database—worldwide.

Abstract of FR2692259, Aromatisation of 2-4C hydrocarbons—using a fixed-mobile-catalytic bed process, Publication date: Dec. 17, 1993, Inventor: Alario et al., esp@cenet database—worldwide.

Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.

Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor. Balthasart et al., esp@cenet database—worldwide.

Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2-dichloroethane from reactor, Publication date: Oct. 6, 2006, Inventor: Balthasart et al., esp@cenet database—worldwide.

Abstract of IT1255246, Process for the preparation of dinitrodiphenylmethanes, Publication date: Oct. 20, 1995, Applicant: Enichem Spa et al., esp@cenet database—worldwide.

Abstract of IT1255358, Process for the synthesis of 1, 4-butanediol, Publication date: Oct. 31, 1995, Inventor: Marco, esp@cenet database—worldwide.

Abstract of JP2142740, Production of fluoroalcohol, Publication date: May 31, 1990, Inventor: Tsutomu et al., esp@cenet database—worldwide.

Abstract of JP2144150, Chemical process and catalyst used therefore, Publication date: Jun. 1, 1990, Inventor: Deidamusu et al., esp@cenet database—worldwide.

Abstract of JP4305542, Production of halogenated hydrocarbon compounds, Publication date: Oct. 28, 1992, Inventor: Shinsuke et al., esp@cenet database—worldwide.

Abstract of JP6172225, Method for fluorinating halogenated hydrocarbon, Publication date: Jun. 21, 1994, Inventor: Takashi et al., esp@cenet database—worldwide.

Abstract of JP6206834, Production of tetrachloroethanes, Publication date: Jul. 26, 1994, Inventor: Toshiro et al., esp@cenet database—worldwide.

Abstract of JP8266888, Method for decomposing aromatic halogen compound, Publication date: Oct. 15, 1996, Inventor: Yuuji et al., esp@cenet database—worldwide.

Abstract of JP2001031605, Production of 3-hydroxy-1-cycloalkene, Publication date: Feb. 6, 2001, Inventor: Hideo et al, esp@cenet database—worldwide.

Abstract of JP2004075683, Method for producing optically active halogenohydroxypropyl compound and glycidyl compound, Publication date: Mar. 11, 2004, Inventor: Keisuke et al., esp@cenet database—worldwide.

Abstract of JP2004189655, Method for fluorinating with microwave, Publication date: Jul. 8, 2004, Inventor: Masaharu et al., esp@cenet database—worldwide.

Abstract of JP2005075798, Method for Producing adamantyl ester compound, Publication date: Mar. 24, 2005, Inventor: Norihiro et al., esp@cenet databas—worldwide.

Abstract of JP2005082563, Method for producing 1, 3-adamantanediol, Publication date: Mar. 31, 2005, Inventor: Norihiro et al., esp@cenet database—worldwide.

Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.

Abstract of JP2005254092, Method of manufacturing alkynes, Publication date: Sep. 22, 2005, Inventor: Shirakawa Eiji, esp@cenet database—worldwide.

Abstract of JP2006151892, Preparation method of alcohol derivative, Publication date: Jun. 15, 2006, Inventor: Baba Akio et al., esp@cenet database—worldwide.

Abstract of JP2006152263, Organic-inorganic hybrid-type mesoporous material, method for producing the same, and solid catalyst, Publication date: Jun. 15, 2006, Inventor: Junko et al., esp@cenet database—worldwide.

Abstract of JP2006193473, Aryl polyadamantane derivative having carboxy or acid anhydride group and method for producing the same, Publication date: Jul. 27, 2006, Inventor: Yasuto et al., esp@cenet database—worldwide.

Abstract of JP2006231318, Phosphorus containing macromolecule immobilizing palladium catalyst and method for using the same, Publication date: Sep. 7, 2006, Inventor: Osamu et al., esp@cenet database—worldwide.

Abstract of JP2006263567, Optical resolution method of optical isomer and optical resolution device, Publication date: Oct. 5, 2006, Inventor: Yoshikazu et al., esp@cenet database—worldwide.

Abstract of JP2006265157, Method for catalytically activating silicated nucleating agent using phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 11, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.
U.S. Office Action from U.S. Appl. No. 11/254,438 dated Jan. 24, 2007.
U.S. Office Action from U.S. Appl. No. 11/254,438 dated Nov. 1, 2007.
U.S. Office Action from U.S. Appl. No. 10/893,418 dated Jan. 2, 2008.
U.S. Office Action from U.S. Appl. No. 10/893,418 dated Jun. 14, 2007.
U.S. Office Action from U.S. Appl. No. 11/091,130 dated Oct. 3, 2007.
U.S. Office Action from U.S. Appl. No. 10/365,346 dated Jun. 12, 2006.
U.S. Office Action from U.S. Appl. No. 11/103,326 dated Aug. 31, 2007.
U.S. Office Action from U.S. Appl. No. 11/103,326 dated Dec. 6, 2006.
U.S. Office Action from U.S. Appl. No. 11/098,997 dated Nov. 20, 2008.
U.S. Office Action from U.S. Appl. No. 12/215,326 dated Feb. 10, 2009.
U.S. Office Action from U.S. Appl. No. 10/430,240 dated Mar. 6, 2006.
U.S. Office Action from U.S. Appl. No. 10/369,148 dated Oct. 16, 2006.
U.S. Office Action from U.S. Appl. No. 10/369,148 dated Mar. 14, 2006.
U.S. Office Action from U.S. Appl. No. 10/894,165 dated Aug. 16, 2006.
U.S. Office Action from U.S. Appl. No. 12/080,594 dated Dec. 22, 2008.
U.S. Office Action from U.S. Appl. No. 11/703,358 dated Jun. 11, 2008.

* cited by examiner

HYDROCARBON CONVERSION PROCESS IMPROVEMENTS

CROSS-REFERENCE TO RELATED APPLICATIONS

This application is a continuation of U.S. patent application Ser. No. 12/692,831 filed Jan. 25, 2010 now U.S. Pat. No. 7,838,708, which is a continuation of U.S. patent application Ser. No. 11/098,997 filed Apr. 5, 2005 now abandoned, which is a continuation-in-part of U.S. patent application Ser. No. 10/430,240 filed Aug. 19, 2003 now U.S. Pat. No. 7,161,050, which is a continuation-in-part of prior application Ser. No. 10/365,346 filed Feb. 12, 2003 now abandoned, which is a continuation of prior application Ser. No. 10/298,440 filed Nov. 19, 2002, abandoned, which is a continuation-in-part of prior application Ser. No. 10/208,068, filed Jul. 29, 2002, abandoned, which is a continuation-in-part of prior application Ser. No. 10/054,004 filed Jan. 24, 2002, now U.S. Pat. No. 6,486,368, which is a continuation-in-part of prior application Ser. No. 09/951,739, filed Sep. 11, 2001, now U.S. Pat. No. 6,465,696, which is a continuation-in-part of application Ser. No. 09/886,078 filed Jun. 20, 2001, now U.S. Pat. No. 6,472,572.

CLAIM OF PRIORITY

Applicant claims priority based on provisional patent application Ser. No. 60/559,844, filed Apr. 6, 2004.

TECHNICAL FIELD

This invention relates generally methods and apparatuses for synthesizing olefins, alcohols, ethers, and aldehydes from alkanes, alkenes, and aromatics, and more particularly to specific improvements in the methods and apparatuses disclosed in the patents and patent applications identified herein.

BACKGROUND AND SUMMARY OF THE INVENTION

The present application comprises a continuation-in-part of application Ser. No. 10/430,240, the disclosure of which is incorporated herewith by reference as if set forth herein. The present invention comprises specific improvements in and to the methods and apparatuses disclosed and described in the patents and patent applications identified herein, specifically including:
Safety Improvements;
Use of Alternative Feedstocks;
Process Simplification;
Improvements to the Halogenation Step;
Improvements to the Reproportionation Step;
Improvements to the Solid Oxide Reaction;
Improvements to Solid Oxide Regeneration;
Improvements in Separations;
Maintenance;
Start-up;
Shut-down;
Materials of Construction.

DETAILED DESCRIPTION

Safety Improvements:
1. The safety of the process may be improved by shipping the halogen in solid halide form. Some specific variations include:
   a. The solid may be one of the solids that will be used in the process. One advantage is that separate halide liberation equipment may be avoided. The solid may be regenerated using air, oxygen, and/or oxygen-containing gas in the process equipment.
   b. The solid may also be a solid that is not used in the process, but rather a solid which is inexpensive, relatively non-toxic, able to liberate halide at lower temperature, liberates halide with heating rather than oxidation, less hygroscopic, less corrosive in solid form, less corrosive to regenerate, less volatile, more dense, containing a higher halogen content, disposable, and/or otherwise more convenient for shipping. Examples include:
      i. Copper chloride, copper bromide, or copper iodide may be used for the shipment of chlorine, bromine, or iodine due to relatively low cost of copper relative to some other materials.
      ii. Copper halides may be used for shipment for processes in which the reactive solid contains nickel, chromium, lead, cobalt, or other potentially toxic elements.
      iii. Calcium bromide may be used to ship bromine for use in a process using a cobalt-containing metal oxide since cobalt bromide readily forms highly hydrated species.
      iv. Copper chloride, copper bromide, or copper iodide may be used for the shipment of chlorine, bromine, or iodine since copper halides may be easily regenerated with air, oxygen, or oxygen containing gas at temperatures below those required to regenerate other solids.
      v. Copper (II) bromide may be used to ship bromine since bromine may be liberated by heating without oxygen.
      vi. Copper bromide may be used to ship halide for processes using iron-containing materials since iron bromide is hygroscopic, potentially volatile, and potentially corrosive.
      vii. Pure copper halide may be used to ship halide for processes using a supported metal oxide. Such a choice will eliminate the need to transport the inert support.
      viii. Carbon tetrabromide may be used with combustion of this material either in dedicated equipment or within a process unit, generating bromine and carbon dioxide. Such a solid is disposable, thereby eliminating the requirement of returning the solid oxide to a processing facility.
   c. The solid may also be a solid that is not used in the process so that the solid used may be shipped in oxide form, which may be more stable, less likely to sinter, dissolve, adsorb (or absorb) water (or other contaminants), or fracture.
   d. As the solid used in the process can hold substantially more bromine than the optimum level for use in the process, the solid could be shipped to an operating facility with a relatively high level of bromine that could be used to make up the small amount of bromine that may be lost during normal operation of the process.
2. The safety of the process may be improved by shipping the halogen in liquid halide form. The use of liquid may minimize solids handling operation and associated particulate hazards. Liquid may also be easier to handle.
   a. Specifically, boron tribromide may be used with oxidation to boron oxide liberating bromine.
3. The safety of the process may be improved by shipping the halogen in liquid alkyl halide form. The use of liquid halides may minimize solids handling operation and associated particulate hazards. The use of liquid halides may also be easier to handle. The shipment of alkyl halide may be particularly useful for the startup of the plant and may also provide a convenient and safe way to introduce make-up halide.

4. The safety of the process may be improved by the placement of hygroscopic metal halides in selected reactors provided with a sink for water in the event of a process upset. Many metal halides are hygroscopic and will react with water to form hydrates, minimizing corrosion.
  a. The metal halides may be selected and placed so that they are molten in the hydrated form and easily removed.
  b. The metal halides may be selected based on a low melting temperature so that they can be pumped into the process in the event of an upset.

5. The bromine inventory may be reduced by utilization of the bromine separation apparatus (typically following the regeneration reactor) as the reservoir for bromine for introduction into the alkane bromination reactor or other necessary step involving bromine. This reservoir of liquid bromine will have sufficient capacity to maintain adequate pump priming and allow bromine to be pumped as a liquid rather than using more costly compressors.

6. Reactive metal oxide traps at all process vents for use in normal and emergency operations may be used to insure against release of any and all organic-bromides. These metal oxides may be regenerated to recover bromine.

7. The safety of the process may be enhanced by the use of a solid oxide to dispose of halogenated organic streams and recovery of halide by conversion to carbon dioxide, water, and solid halide. The solid oxide may be regenerated by reacting the solid halide with oxygen, liberating halogen for recycle to the process.
  a. One example is the use of $CuO$ or $CuZrO_3$ to convert vinyl bromide to carbon dioxide, water, coke, and $CuBr$ or $CuBrZrO_2$.

Use of Alternate Feedstocks

The above-identified processes may be useful and particularly valuable with feedstocks containing otherwise difficult to separate components. The halogenation chemistry may facilitate the reactive separation of various streams including:

1. The use of steams containing alkane and olefin of the same carbon number.
  a. The olefin may be converted with molecular halogen or solid halide to the 1,2-dihalide for use as a feedstock to an epoxide process. The 1,2-dihalide will be easy to separate from the alkane. Examples include:
    i. Converting the propylene in a stream containing propane and propylene to 1,2-dibromopropane and subsequently to propylene oxide. The 1,2-dibromopropane is formed by reacting the mixed hydrocarbon stream with bromine, most preferably at low temperatures where little appreciable reaction with propane occurs. Separation of propane from propylene is required in many existing plants including ethylene plants and is considered one of the most difficult separations in the chemical industry.
  b. The olefin may be converted with wet halogen to halohydrin for use as a feedstock to an epoxide process. The halohydrin will be easy to separate from the alkane. Examples include:
    i. Converting the propylene in a stream containing propane and propylene to the bromohydrin and subsequently to propylene oxide. The propylene is converted by passing the hydrocarbon stream through bromine water.
  c. The olefin may be converted with hydrogen halide to form the monohalide for use as a feedstock in an olefin, alcohol, epoxide, aldehyde, ketone, or other process. The halide will be easy to separate from the alkane. Examples include:
    i. Converting olefin in a gasoline feed to alkyl halide by reacting with hydrogen halide to form alkyl halide. The alkyl halide can be easily removed, leaving olefin-depleted gasoline.
    ii. Converting butenes to butyl halides in a mixed feed of butanes and butenes. The butyl halides may be coupled to products containing eight carbon atoms for use in gasoline.

2. The use of streams containing branched and linear alkanes resulting in product streams enriched in branched and/or linear molecules.
  a. Branched alkanes containing tertiary carbon may be selectively halogenated to alkyl halide and separated, leaving a stream enriched in linear alkane. Examples include:
    i. Depletion of the branched content of detergent-range alkanes by reaction with halide, resulting in greater reactivity with the branched alkanes to branched alkyl halides. Following separation of the branched halides, the remaining stream is enriched in linear alkane. The stream rich in branched halides may be dehydrohalogenated either catalytically or using a solid oxide to create a stream rich in branched olefin for hydroformylation and conversion to branched alcohols.
  b. Branched alkanes containing tertiary carbon may be selectively halogenated to alkyl halide. Following separation, the halide stream will inevitably contain some non-branched halides. By selectively dehydrohalogenating the tertiary halides, a stream containing a very high fraction of branched olefins can be separated from the remaining halides. The selective dehydrohalogenation may be conducted thermally, using a catalyst at temperatures below those required for secondary alkyl halide dehydrohalogenation, or using a solid oxide catalo reactant at temperatures below those required for secondary alkyl halide dehydrohalogenation. Dehydrohalogenating the remaining halides will leave a stream enriched in linear olefins.

3. The use of streams containing multiple types of branched molecules resulting in product streams enriched or depleted in molecules containing a certain type or amount of branching:
  a. Streams containing linear, mono-branched, and multiply-branched alkanes may be enriched or depleted in multiply-branched product by halogenating the multiply-branched alkanes to multiply-halogenated separation. The multiply-halogenated and/or mono-halide species may be easily separated. Following the desired separation of the non-halogenated, mono-halogenated, and multi-halogenated species, and dehydrohalogenation of the halides, the various streams may be recombined to generate the desired branching composition.
  b. Streams containing branched alkanes with and without multiple branching at a single carbon (quaternary carbon) may be depleted in these quaternary carbon-containing species by halogenating the branched alkanes without the quaternary carbon, separating these halides, and dehydrohalogenating. The result will be streams rich in branched olefins without quaternary carbon and alkanes with quaternary carbon.

4. The use of streams containing trace amounts of impurities that are more reactive than the desired alkane reactant:
  a. Alkane streams containing aromatics, alcohols, olefins, aldehydes, ketones, sulfides, sulfates, or other reactive molecules may be halogenated at low temperature to selectively halogenate the impurities for removal.
b. Streams of mixed alkanes (e.g. natural gas, refinery streams) may be differentially halogenated based on differing rates of halogenation and subsequently reacted with metal oxides at lower temperatures where the non-halogenated alkanes would pass through without reaction.

5. The use of streams of mixed alkane and olefin in coupling processes. Streams containing alkanes and olefins may be used to produce products of higher carbon number. Several process variations may be employed:
   a. A process with:
      i. Olefin hydrohalogenation in the presence of the alkane;
      ii. Separation of the resulting alkyl halide from the alkane;
      iii. Halogenation of Alkane;
      iv. Separation of the resulting alkyl halide from the alkane;
      v. Recycle of alkane;
      vi. Feed of the alkyl halide to the coupling reactor.
   b. Several variations of (a) may be employed:
      i. Specifically, step ii (separation of alkyl halide after hydrohalogenation) may or may not be omitted.
      ii. The alkane may or may not be separated from the alkyl halide (step iv).
      iii. Reproportionation chemistry may or may not be employed.
      iv. The olefin and alkane may be separated at the beginning of the process.
      v. Halogenation may precede hydrohalogenation, particularly if high temperature is employed to hinder addition of halogen to the olefin.
      vi. The hydrogen halide used for hydrohalogenation may or may not be the same formed in the halogenation step.

Process Simplification

1. The halogenation and solid oxide reaction steps may be conducted in the same unit:
   a. The halogenation and solid oxide reaction may be simultaneous.
   b. The halogenation may occur first by varying the contacting of the hydrocarbon, halogen, and solid oxide.
2. The halogenation, solid oxide reaction, and solid oxide regeneration may be conducted in the same unit by introducing hydrocarbon and oxygen to a solid halide or solid halide-oxide combination. The oxygen will regenerate the solid halide generating hydrocarbon halide and solid oxide, the hydrocarbon halide will react with the oxide, generating product. Variations include:
   a. Periodic switching of the direction of feed to the reactor to minimize halogen migration from the reactor. Examples include:
      i. Coupling methane to heavier products by cofeeding methane and oxygen over a metal-halide-containing solid.
3. The solid oxide reaction and product separation may be conducted simultaneously when the product is lighter then the reactant the reaction is conducted in a liquid phase reactor under conditions where the product is a vapor and leaves the reactant mixture.
4. Reacting the halide-containing regeneration effluent with olefin to form dihaloalkanes to reduce the energy required for and equipment size in the halide recovery.
5. Reacting the alkane over selected metal-halides in the regeneration step to form the alkyl-halide and a metal-hydride. This would also be a safety improvement and eliminate the need for halogen separation. Materials include but are not limited to halides of boron, nickel, iron, and their mixtures as well as carbon based materials (e.g. C60).
6. Operation of the halogenation process at high halogen:alkane ratio for the feed at temperatures and pressures to maximize the production of monohalo-alkanes at 100% alkane conversion. The alkane feed may be mixed. The products which will contain multiply-halogenenated species and haloacid which may be passed directly over a metal oxide bed to produce a mixture of products dependent upon the reaction conditions will be produced which will be condensed together and separated in the liquid phase by a combination of distillation and phase separation.
7. The use of a hydrogenation step to recover the over-halogenated products by reducing the halogenation to the desired degree. The use of such a step will allow for higher per-pass conversion in the halogenation step. Catalysts may be used, including but not limited to Pd, Pt, Ru, Ni, Au, Cu, and their alloys.
8. Controlling the amount of hydrogen halide added to a metal oxide reactor in order to generate the heat required for an endothermic reaction.
9. The use of hydrogen halide formed in the halogenation step for conversion of byproducts or products into more useful compounds.
   a. For example, HBr could be used to hydrobrominate vinylbromide, a common undesirable by-product resulting from HBr elimination from dibromoethane back to same (or any higher vinylbromide equivalent to the corresponding dibromoalkane). In another example, HBr could be used in the acidic cleavage of ethers into alcohols and alkylbromides, the former increasing the yield of the desired alcohol product and the latter being recycled to the educt stream for reaction on the metal oxide.

Improvements to the Halogenation Step

1. Improvements in selectivity to desired multiply-halogenated isomers through isomerization of the multiply-halogenated species formed by halogenation. Examples include:
   a. Forming dihalides dehydrohalogenating the dihalides, and rehydrohalogenating to form the desired isomers. The rehydrohalogenation may be conducted using process conditions different from the initial halogenation to enhance yield of the desired isomer. The process conditions varied may include temperature, pressure, and catalyst. Some examples include:
      i. Halogenating ethane so that it contains mixed halides including 1,1 and 1,2-dihaloethanes. Dehyrohalogenating the dihaloethanes, and rehydrohalogenating to enrich the 1,2-dihaloethane content.
      ii. Halogenating propane so that it contains mixed halides including 1,1, 2,2, 1,3, and 1,2-dihalopropanes. Dehydrohalogenating the dihalopropanes, and rehydrohalogenating to enrich the 1,2-, 2,2-, 1,3, or 1,1-isomer content.
      iii. Halogenating butane so that it contains mixed dihalides. Dehydrohalogenating, and rehydrohalogenating to enrich the 2,2- or 2,3-isomer content. The 2,2- or 2,3-isomer may be reacted with a metal oxide to make methyl-ethyl ketone.
      iv. Halogenating butane so that it contains mixed tetrahalides. Dehydrohalogenating, and rehydrohalogenating to enrich the 1,2,3,4-isomer content.
      v. Halogenating cyclohexane so that it contains mixed halides including 1,1, 1,2, 1,3, and 1,4-dihaloisomers.

Dehyrohalogenating, and rehydrohalogenating to enrich the 1,1, 1,2, 1,3, and 1,4-dihaloisomer content.

2. Enrichment in the primary halide content of a stream of mixed halide isomers by separating primary halides from other halide isomers. Dehydrohalogenating the other isomers, rehydrohalogenating the resulting olefins to produce a stream enriched in primary halide isomers, and returning the resulting stream to the primary halide separation step. Some variations include:

a. Using selective dehydrohalogenation of the non-primary isomers to form easily separated olefin and hydrogen halide.
  b. Using distillation to separate the primary and other isomers.
  c. Using adsorption to separate the primary and other isomers.
  d. Using a shape-selective catalyst to rehydrohalogenate the olefin, enhancing primary halide yield.

3. The use of multiple halogens to create the desired halide isomer. One halogen may be used to halogenate the hydrocarbon and be replaced by another.

4. The use a membrane reactor with halogen on one side and alkane on the other to improve selectivity to the desired halide isomer. This reactor design may improve monohalogenation, dihalogenation, and/or primary halogenation selectivity.

5. Operation of the halogenation reaction at high halogen:alkane ratio to improve conversion may result in unconverted halogen. Photoactivation of the unconverted halogen may be used at low temperature in a solid oxide bed to allow full recovery of all the halogen.

Improvements to the Reproportionation Step

In many processes, the overhalogenated species may be recycled to a point in the process where they are converted to the desired degree of halogenation or less than the desired degree of halogenation. The change in degree of halogenation is termed "reproportionation," and allows for the use of the carbon and hydrogen in the overhalogenated species, thus reducing feedstock loss and perhaps also allowing greater economic per-pass yield.

Several Improvements Include:

1. A low-temperature reproproportionation step, in which the halogen is redistributed among over-halogenated species, resulting in the formation of optimally halogenated species and additional very highly halogenated species.
  a. An example is a mixture of dibromomethane, tribromomethane, and tetrabromomethane are allowed to react, producing a stream enriched in methyl bromide and tetrabromomethane.

2. A low-temperature reproportionation step, in which the halogen is redistributed among over-halogenated species, resulting in the formation of optimally halogenated species and additional very highly halogenated species. The yield of optimally halogenated species is maximized by conducting this reproportionation under temperature, pressure, and process conditions such that the reproportionation is conducted in the liquid phase while the optimally halogenated species is predominantly in the vapor phase.
  a. An example is: a mixture of liquid dibromomethane, tribromomethane, and tetrabromomethane are allowed to react in the presence of a catalyst at about 30 C. As the bromine is redistributed and methyl bromide is formed, much of the methyl bromide leaves the solution and enters the vapor phase.

3. The conversion of over-halogenated hydrocarbon to carbon black or other carbon material and halogen. The carbon material may be sold and the halogen may be recycled to the process.

4. The reproportionation of overhalogenated hydrocarbon with another hydrocarbon or halohydrocarbon. Such a process may allow the recovery of the desired hydrocarbon with a loss of a less desirable material.
  a. For example, dibromomethane is reacted with propane to make methyl bromide and brominated propanes. Ideally, one propane molecule can be used to convert eight dibromomethane molecules to methyl bromide. The bromine can be recovered from the brominated propane through thermal decomposition, oxidation, reaction with solid oxide, or other means.

Improvements to the Solid Oxide Reaction

1. A method of contacting water with alkyl halide and metal oxide in a multi-phase reactor with alkyl halide, solid oxide and optional diluent present at the bottom of the reactor with refluxing water present in a zone above the reactant mixture.

2. The product yield may be increased and process corrosivity may be reduced by conducting the solid oxide reaction in a liquid phase with water present to remove metal halide as it is formed. A specific example is:
  a. The reaction is conducted in a vessel containing liquid alkyl halide, liquid water, water vapor, and solid. The water vapor condenses at the top of the reactor or is returned from an external condenser and settles through the metal oxide and alkyl halide containing phase. The water dissolves metal halide as it passes through the alkyl halide phase. The solid oxide may be supported on a plate to keep it out of the liquid water phase. The water and metal halide passes into a separate liquid phase at the bottom of the reactor where some of the water is vaporized. Variations include:
    i. A batch reactor.
    ii. A continuous reactor in which alkyl halide, metal oxide, and water (or steam) are added continuously and metal halide solution is removed continuously to a regeneration reactor where it is dried and regenerated.
    iii. The use of precipitation to remove metal halide from the metal halide solution. By reducing the temperature of the solution, some of the metal halide will precipitate for regeneration. The depleted metal halide solution may be recovered by filtration, centrifugation or other solids-liquid separation methods and recycled to the reactor. Recovered solids can be dried and regenerated to metal oxide and bromine.

3. The liquid phase performance of a reactor may be improved by adding a diluent. The diluent may be, but is not limited to alkanes that are readily separated from the products and reactants.

4. The yield to desired product may be improved by introducing the stream containing hydrocarbon halide to the metal oxide in stages.

5. The yield to desired product may be improved by providing a feed of solid to a fluidized bed reactor that includes some partially or completely spent material. Spent is defined as solid with no remaining oxygen (donation) capacity or bromine capacity.

6. The yield to desired product may be improved by providing a feed of solid to a fluidized bed reactor that includes some partially coked material.

7. The solid oxide reaction may be conducted in a series of switched fixed beds, some of which are undergoing regeneration at any given time.

8. In a process for the production of olefins, the di-halogenated species may be at least partially converted to olefin using certain solids. Some examples include:
   a. The reaction of silver metal with 1,2-dibromoethane to form ethylene and silver bromide. The silver bromide may be decomposed to silver and bromine using heat or electromagnetic radiation.
   b. The reaction of copper (I) bromide with 1,2-dibromethane to form ethylene and copper(II) bromide. The copper (II) bromide may be decomposed to copper (I) bromide and bromine using heat.
   c. The reaction of 1,2-dibromomethane with a metal oxide to form ethylene, carbon dioxide, water, and metal bromide. The metal bromide may be regenerated by reaction with oxygen.

Improvements to Solid Oxide Regeneration

1. Varying the temperature of solid oxide prior to oxygen introduction to change the particle size of the solid oxide to a more desirable distribution.
   a. By raising the temperature, particularly to that above the regeneration onset temperature, prior to introduction of oxygen or air, the metal oxide obtained after regeneration may be reduced in the amount of fines or agglomerates it contains.
   b. By introducing oxygen at low temperature, particularly at that below the regeneration onset temperature, the metal oxide obtained after regeneration may be reduced in the amount of fines or agglomerates it contains.
2. Increasing the temperature of solid oxide prior to oxygen introduction to dehydrogenate or desorb adsorbed hydrocarbon, reducing the amount of water and possibly carbon oxides generated in regeneration, thus reducing corrosivity and simplifying halide purification.
3. Performing a separate oxidation, particularly at low temperature, to remove adsorbed hydrocarbon reducing the amount of water and carbon oxides generated in regeneration, thus reducing corrosivity and simplifying halide purification.
4. Introducing water to the solid halide to change the particle size of the resulting solid oxide to a more desirable distribution.
   a. The water may be introduced in the gas phase.
   b. The water may be introduced in the liquid phase.
   c. The water may be introduced concurrently with or prior to the introduction of oxygen.
   d. The hydrated solid may be allowed to settle and agglomerate.
   e. The hydrated solid may be subjected to intense fluidization to break apart agglomerates.
   f. A slurry or aqueous phase may be formed and dried in a manner to form the desired particle size. In particular, spray drying may be used.
5. Dissolving the active metal halide to separate it from impurities, and then converting metal halide to metal oxide.
6. The use of very high temperature regeneration to remove impurities. In particular, chlorine may be removed from metal bromide in this manner.
   a. The combination of high temperature with heating of the solid halide prior to oxygen introduction may be particularly useful. In the case of metal bromides, this methodology may allow the removal of chlorine as ClBr or $Cl_2$.
7. The reduction of the solid halide with hydrogen or other reducing agent to remove impurities. The reduced material may be reoxidized with oxygen, air, or other oxygen containing gas.

Improvements in Separations

1. Separation of halogen from nitrogen, oxygen, and other non-condensibles using solid adsorbents. The solid adsorbents will adsorb the halogen, which can be removed by heating the solid or reducing the pressure. The adsorbents may be, but are not limited to:
   a. Molecular sieves;
   b. Mesoporous materials;
   c. Zeolites;
   d. Silica;
   e. Alumina;
   f. Aluminosilicates;
   g. Magnesia;
   h. Activated carbon;
   i. Metal bromides;
   j. Metal oxides;
2. Separation of halogen from nitrogen, oxygen, and other non-condensibles using reactive solid adsorbents. The solid reactive adsorbents will react with the halogen, forming a new chemical composition, from which the halogen can be removed by heating the solid or reducing the pressure, regenerating the solid. The reactive adsorbents may be, but are not limited to:
   a. Copper (I) bromide;
   b. Iron (II) bromide;
   c. Silver bromide;
   d. Carbon;
   e. Carbon, particularly fullerenes or nano-tubular carbon.
3. Removal of water from halogen by passing the mixed stream over metal halides or metal halide hydrates which may be supported or unsupported. The metal halides will form hydrates and the metal halide hydrates will form more highly hydrated species. The water can be liberated and starting material can be regenerated by heating.
4. Methods of removing trace amounts of halogen from product streams using reactive solids, which may or may not be regenerable. Some specific reactive solids include, but are not limited to:
   a. Copper (II) oxide;
   b. Silver;
   c. Copper;
   d. Lithium;
   e. Magnesium;
   f. Alkali metals.
5. Removal of residual halogen from streams by reaction with olefins. Specific examples include:
   a. Reacting with ethylene or propylene to form dihaloalkane, which can be converted to epoxide.
   b. Reacting with a heavy multiple-olefin to form highly halogenated species from which the halide can be recovered.
6. Removal of residual hydrocarbon halide from streams by reaction with reactive solids Some specific reactive solids include, but are not limited to:
   a. Copper (II) oxide;
   b. Silver;
   c. Copper;
   d. Lithium;
   e. Magnesium;
   f. Alkali metals.
7. Separation of primary, secondary, and/or tertiary alkyl halides by selective dehydrohalogenation of selected species, separation of the olefin and hydrogen halide from the remaining alkyl halide, and recombination of the hydrogen halide and olefin to form alkyl halides. Examples include, but are not limited to:
   a. Separation of primary from secondary alkyl halides by selectively dehydrohalogenating the secondary alkyl halides to olefin and hydrogen halide, separation of the olefin and hydrogen halide from the primary halide, and recombination of the hydrogen halide and olefin to form secondary and possibly primary halide.
  b. Separation of primary and secondary alkyl halides from tertiary alkyl halides by selectively dehydrohalogenating the tertiary alkyl halides to olefin and hydrogen halide, separation of the olefin and hydrogen halide from the primary and secondary alkyl halide, and recombination of the hydrogen halide and olefin to form alkyl halide.
8. Removal of sulfur-containing compounds from a hydrocarbon feed by reacting the feed with dry halogen to form sulfur, which can be removed as a solid from the sulfur-depleted hydrocarbon and hydrocarbon halide stream.
9. Removal of sulfur-containing compounds from a hydrocarbon feed by reacting the feed with dry halogen to form sulfur, which can be removed as a solid from the sulfur-depleted hydrocarbon and hydrocarbon halide stream.
10. Removal of carbon dioxide from a stream by reacting with a carbonate-forming material such as calcium oxide. The carbonate may be used in a hydrogen-halide recovery section of the plant. The carbonate will react with hydrogen halide, liberating water and carbon dioxide and producing solid halide, which can be regenerated and recycled to the carbon dioxide separation section.
11. Removal of arsenic, mercury, heavy metal-containing compounds from a hydrocarbon feed by reacting the feed with dry halogen to form solid metal compounds, solid metal halides or halogenated metal hydrocarbons, which can be easily separated.
12. Removing adsorbed product from the solid by rinsing with a compound that is easily separated from the product. Such a rinsing agent may be pentane or other alkane.
13. Removing adsorbed product from the solid by steam distillation.

Maintenance

1. A method of removing coke from reactors by reacting with bromine to form volatile carbon bromides. The carbon bromides may be used in the process in a reproportionation step, thus producing product from the coke.
2. A method of removing coke from reactors by reacting with hydrogen bromide to form volatile hydrocarbon bromides. The carbon bromides may be used in the process in a reproportionation step, thus producing product from the coke.

Start-Up

1. Starting the process with some or all of the solid in the halide or partially halogenated form may provide a number of benefits including:
  a. The ability to start the regeneration reactor early in the start up sequence.
  b. Reduction in the amount of oxygen carried over into the bromine separation unit.
  c. Reduction in the heat generated in the metal oxide reactor or hydrogen halide neutralization step.
  d. Reduction in the amount of adsorbed hydrocarbon and thus reduction in the amount of water and carbon dioxide generated in the regeneration unit.
  e. Reduction in unfavorable changes in the particle size distribution of the metal oxide.
  f. Improvement in the packing of a fixed bed reactor.
  g. Providing a hygroscopic metal halide to reactively remove water during upsets.
2. Starting the process with some or all of the solid in the oxide or partially oxygenated form may provide a number of benefits including:
  a. The ability to start the solid oxide reactor early in the start up sequence.
  b. Reduction in the amount of bromine generated in the regeneration reactor.
  c. Reduction in the heat generated in the metal oxide reactor or hydrogen halide neutralization step.
  d. Reduction in the amount of adsorbed hydrocarbon and thus reduction in the amount of water and carbon dioxide generated in the regeneration unit.
  e. Reduction in unfavorable changes in the particle size distribution of the metal
  f. Improvement in the packing of a fixed bed reactor.
  g. Providing a hygroscopic metal halide to reactively remove water during upsets.
3. Starting the process with a solid which has undergone a number of regeneration cycles may offer benefits including:
  a. Reduction in byproducts.
  b. Improved chemical and thermal stability of reactors
4. Starting the process with the halogen present in part or completely as alkyl halide may be desirable for a number of reasons including:
  a. Less free halogen present during start-up.
  b. Ability to start the halide separations section early in the start-up sequence with no hydrogen halide or water present.

Shut-Down

1. Stopping the process with the halide in metal halide and/or alkyl halide form may improve safety, reduce corrosion, and improve maintenance accessibility.
2. Introducing reactive components into certain sections of the plant may provide a sink for halogen or hydrogen halide, improving safety, reducing corrosion and improving accessibility. An example of such a component is olefin.

Materials of Construction

1. The reactors for alkane halogenation and metathesis consisting of materials to minimize corrosion including but not limited to:
  a. Stainless steel;
  b. Silicon carbide;
  c. Glass lined steel;
  d. Titanium;
  e. Carbon fiber.
2. Process components operating at temperatures below 300 C. constructed from:
  a. Teflon;
  b. Glass.

What is claimed is:

1. A method comprising:
providing a first quantity of alkane;
providing a quantity of bromine;
reacting the first quantity of alkane with the quantity of bromine to form alkyl monobromides, hydrogen bromide, and alkyl polybromides;
providing a second quantity of alkane;
reacting the second quantity of alkane with the alkyl polybromides to form additional alkyl monobromides;
reacting the alkyl monobromides and the additional alkyl monobromides with a metal oxide to form a metal bromide and at least one reaction product selected from the group consisting of an alcohol and an ether;
contacting the metal bromide with oxygen or air to regenerate the metal oxide and to form bromine; and
recycling the bromine.

2. The method of claim 1 wherein the first and second quantities of alkane comprise at least one alkane selected from the group consisting of methane, ethane, propane, butane, and isobutane.

3. The method of claim 1 wherein the first and second quantities of alkane comprise methane.

4. The method of claim 1 wherein the alkyl polybromides comprise $CH_2Br_2$. and the alkyl monobromides comprise $CH_3Br$.

5. The method of claim 1 wherein the reaction product comprises methanol.

6. The method of claim 1 wherein the reaction product comprises dimethyl ether.

7. The method of claim 1 wherein the alkyl monobromides and the additional alkylmonobromides are reacted with hydrogen bromide and the metal oxide to form the metal bromide and the at least one reaction product.

8. The method of claim 1 wherein the second quantity of alkane is reacted with the alkyl polybromides in the presence of an electrophilic catalyst.

9. A method comprising:
providing a first quantity of alkane;
providing a quantity of bromine;
reacting the first quantity of alkane with the quantity of bromine to form alkyl monobromides, hydrogen bromide, and alkyl polybromides;
providing a second quantity of alkane;
reacting the second quantity of alkane with the alkyl polybromides to form additional alkyl monobromides;
reacting the alkyl monobromides and the additional alkyl monobromides with a metal oxide to form a metal bromide and at least one reaction product selected from the group consisting of an alcohol, an ether, and an olefin;
contacting the metal bromide with oxygen or air to regenerate the metal oxide and to form bromine; and
recycling the bromine.

10. The method of claim 9 wherein the first and second quantities of alkane comprise at least one alkane selected form the group consisting of methane, ethane, propane, butane, isobutane, pentane, hexane, and cyclohexane.

11. The method of claim 9 wherein the first and second quantities of alkane comprise methane.

12. The method of claim 9 wherein the alkyl polybromides comprise at least one alkyl polybromide selected from the group consisting of $CH_2Br_2$, $CHBr_3$, and $CBr_4$ and wherein the alkyl monobromides comprise $CH_3Br$.

13. The method of claim 9 wherein the reaction product comprises methanol.

14. The method of claim 9 wherein the reaction product comprises dimethyl ether.

15. The method of claim 9 wherein the first and second quantities of alkane comprise two or more carbon atoms in their molecular structure and the reaction product comprises an olefin.

16. The method of claim 9 wherein the first and second quantities of alkane comprise ethane and the reaction product comprises at least one reaction product selected from the group consisting of diethyl ether, ethanol, and ethyl acetate.

17. The method of claim 9 wherein the alkyl monobromides and the additional alkylmonobromides are reacted with hydrogen bromide and the metal oxide to form the metal bromide and the at least one reaction product.

18. The method of claim 9 wherein the second quantity of alkane is reacted with the alkyl polybromides in the presence of an electrophilic catalyst.

19. A method comprising:
providing a first quantity of alkane;
providing a quantity of halogen;
reacting the first quantity of alkane with the quantity of halogen to form alkyl monohalides, hydrogen halide, and alkyl polyhalides;
providing a second quantity of alkane;
reacting the second quantity of alkane with the alkyl polyhalides to form additional alkyl monohalides;
reacting the alkyl monohalides and the additional alkyl monohalides with a metal oxide to form a metal halide and at least one reaction product selected from the group consisting of an alcohol, an ether, and an olefin;
contacting the metal halide with oxygen or air to regenerate the metal oxide and to form halogen; and
recycling the halogen.

20. The method of claim 19 wherein the halogen comprises at least one halogen selected form the group consisting of chlorine, bromine, and iodine.

* * * * *